US00PP37511P3

(12) United States Plant Patent
Bull

(10) Patent No.: US PP37,511 P3
(45) Date of Patent: Jun. 30, 2026

(54) ***ECHINACEA* PLANT NAMED 'BullEchipur 118'**

(50) Latin Name: *Echinacea purpurea*
Varietal Denomination: BullEchipur 118

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,107

(22) Filed: Jun. 11, 2025

(65) Prior Publication Data

US 2025/0386749 P1 Dec. 18, 2025

Related U.S. Application Data

(60) Provisional application No. 63/731,837, filed on Jun. 12, 2024.

(51) Int. Cl.
*A01H 5/02* (2018.01)
*A01H 5/12* (2018.01)
*A01H 6/14* (2018.01)

(52) U.S. Cl.
USPC ..... Plt./428
CPC ..... *A01H 6/1448* (2018.05); *A01H 5/02* (2013.01); *A01H 5/12* (2013.01)

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

| | | | | |
|---|---|---|---|---|
| 7,982,110 | B2 | 7/2011 | Ren | |
| PP31,064 | P2 | 11/2019 | Ren et al. | |
| PP35,164 | P2 * | 5/2023 | Ren | A01H 6/1448 Plt./428 |
| PP35,286 | P3 | 7/2023 | Bull | |

OTHER PUBLICATIONS

Wist et al Floral Structure and Dynamics of Nectar Production in *Echinacea pallida* var. *angustifolia* (*Asteraceae*), Int. J. Plant Sci. 169(6):708-722, 2008. (Year: 2008).*

Brookgreen Gardens *Echinacea purpurea* 'PAS702918', retrieved on Aug. 27, 2025 at https://www.brookgreen.ord/plantcollection/name/echinacea-purpurea-pas702918-powwow%25C2%25AE-white, 3 pages.

ThinkPlants Catalog, 2024-2025, retrieved on Sep. 4, 2025 at https://online.flippingbook.com/view/530070179/34/, 6 pages.

* cited by examiner

*Primary Examiner* — June Hwu
(74) *Attorney, Agent, or Firm* — The Webb Law Firm

(57) ABSTRACT

A new and distinct variety of *Echinacea* plant named 'BullEchipur 118' having large pink flowers, good growth habit, more uniform growth, good branching, and good propagation rates.

1 Drawing Sheet

Botanical classification: *Echinacea purpurea.*
Varietal denomination: 'BULLECHIPUR 118'.

BACKGROUND OF THE INVENTION

The present invention relates to a new and distinct cultivar of *Echinacea*, botanically known as *Echinacea purpurea*, and hereinafter referred to by the name 'BullEchipur 118'.

The new *Echinacea* was discovered by the Inventor in August 2021, in a controlled environment in Gönnebek, Germany, as a part of a planned breeding program. The new *Echinacea* was selected on the basis of its large pink flowers, good growth habit, enhanced uniformity, good branching, and good propagation rates.

Asexual propagation of the new cultivar by in vitro culture since September 2021, in Gönnebek, Germany, has shown that the unique features of this new *Echinacea* are stable and reproduced true to type in successive generations.

SUMMARY OF THE INVENTION

The following traits have been repeatedly observed and are determined to be unique characteristics of 'BullEchipur 118'. These characteristics in combination distinguish 'BullEchipur 118' as a new and distinct cultivar:

1. Compact growths
2. Vibrant pink flowers
3. Lots of large flowers
4. More branching habit
5. Very uniform growth
6. Nice green leaves
7. Fast crop time In side-by-side comparisons conducted by the Inventor in Gönnebek, Germany, plants of the new *Echinacea* differed from plants of the female parent, Bul 2020-03, in the following characteristics:

1. More compact
2. More intensive pink flower color
3. Good branching
4. Green small leaves In side-by-side comparisons conducted by the Inventor in Gönnebek, Germany, plants of the new *Echinacea* differed from plants of the male parent, Bul 2020-18, in the following characteristics:

1. More compact
2. More intensive pink flower color
3. More branches

4. Lots of flowers
5. Earlier flowering

Plants of the new *Echinacea* can be compared to the plants of the *Echinacea* cultivar 'PAS702917' which uses the trade name 'PowWow® Wildberry', believed to be unpatented. In side-by-side comparisons conducted by the Inventor in Gönnebek, Germany, plants of the new *Echinacea* differed from plants of the cultivar 'PowWow® Wildberry' in the following characteristics:

1. More compact
2. More branching habit
3. More uniform growth
4. More flowers
5. Cleaner leaves, where clean refers to the consistency of the color (i.e. less brown spots and necroses)
6. Shorter plant

DESCRIPTION OF THE DRAWINGS

The accompanying colored photographs illustrate the overall appearance of the new *Echinacea*, showing the colors as true as it is reasonably possible to obtain in colored reproductions of this type. Colors in the photographs may differ slightly from the color values cited in the detailed botanical description, which accurately describes the colors of the new *Echinacea*.

FIG. 1 comprises a top perspective view of a typical plant of 'BullEchipur 118' under natural light.

DESCRIPTION OF THE PLANT

The cultivar *Echinacea* has not been observed under all possible environmental conditions. The phenotype may vary somewhat with variations in environment such as temperature and light intensity without, however, any variance in genotype.

The aforementioned photographs and following observations and measurements describe plants of the new *Echinacea* that were grown in an outdoor nursery in Gönnebek, Germany. During the production of the plants, temperatures averaged about 18-20° C. Plants used for the photographs and description were about 22 weeks from planting. Color references are made to The Royal Horticultural Society Colour Chart, 2015 version, except where general terms of ordinary dictionary significance are used.

PLANT

Botanical classification: *Echinacea purpurea.*

Parentage: Bul 2020-03 and Bul 2020-18.

Propagation:

*Time to initiate roots.*—About 7 days at about 19-20° C.

*Time to develop roots.*—About 40-50 days at about 18° C.

*Time to produce a finished flowering plant.*—About 12-14 weeks.

*Root description.*—Lots of roots, free-branching, nice, healthy-looking root system.

Plant description:

*Growth rate/vigor.*—Time to grow young plant: About 8-10 weeks. Time from young plant to flowering: About 10-12 weeks.

*Plant habit.*—Compact/upright.

*Plant height.*—40-50 cm.

*Plant width.*—35-40 cm.

*Branching habit.*—Lots of branches, upright.

*Lateral branches.*—Number per plant: 18-25. Length: 2-33 cm. Diameter: 3-8 cm. Internode length: 1-5 cm. Angle: Upright, outwarding. Strength: Strong. Texture: Pubescent. Color: 146C to 184C.

*Foliage.*—Stem Leaves: Length: Young Leaves: Approximately 3-10 cm. Fully Expanded Leaves: Approximately 10-12 cm. Width: 1-5 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A. Lower surface color: 137C. Venation: Type: Cross venulate to longitudinal. Color: Upper surface: 145A. Lower surface: 145B. Rugosity: Weak to Medium. Margin: Entire. Basal Leaves: Length: Approximately 21 cm. Width: 1-5 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A. Lower surface color: 137C. Venation: Type: Cross venulate to longitudinal. Color: Upper surface: 145A. Lower surface: 145B. Rugosity: Weak to Medium. Margin: Entire.

Flowers:

*Bud.*—Stage of opening: Single type blossom. Shape: Elliptic shaped ray florets and tubular disk floret. Diameter: 1-3.5 cm. Length: 1.2-2.5 cm. Color: When closed: 137C. When open: 187A.

*Natural flowering season.*—July-September, 13-14 weeks after planting.

*Inflorescence.*—Form: Single flower. Disc and ray floret arrangement: Single composite flower. Average number per plant: 20-30. Average number per branch: 1-3. Fragrance: None. Diameter: 4-10 cm. Height: 2-4 cm. Diameter of disc: 1.5-4 cm. Receptacle height: 1 cm. Receptacle diameter: 1.5 cm-4 cm. Ray florets: Number per inflorescence: 16-24. Number of short narrow ray florets per inflorescence: 0-10. Arrangement: In 2-3 whorls. Length: 1.5-4.5 cm. Width: 0.9-1.7 cm. Shape: Ellipse. Shape of Apex: Obtuse with shallow (approximately 1 mm) indentations. Shape of Base: Acute. Margin: Entire. Texture: Upper surface: Smooth, glabrous. Lower surface: Rough. Color: When opening: Upper surface: 72C. Lower surface: 73A. At maturity: Upper surface: 72C. Lower surface: 73A. Ground color description: Pink. Attitude: Horizontal to lightly semi-drooping. Profile in Cross Section: Flat. Disc florets: Average Height when Matured: 12-25 mm. Number per inflorescence: Numerous, too many to quantify. Arrangement: In center of receptacle. Length: 8-15 mm. Width: 1-2 mm. Shape: Tubular. Shape of Apex: Sharp. Color of receptacle spine with receptacle bracts: Immature: 187B. At maturity: 187B. Phyllaries: Number per inflorescence: 35-50. Arrangement: In 3-4 whorls. Length: 0.5-1.5 cm. Width: 2-3 mm. Shape: Lanceolate. Shape of Apex: Elongate, oval. Shape of Base: Fused. Margin: Entire. Texture: Upper surface: Rough. Lower surface: Rough. Color: Immature: Upper surface:

NN137C. Lower surface: NN137C. At maturity: Upper surface: NN137C. Lower surface: NN137C.

Reproductive organs:

*Androecium*.—Presence: On disk florets. Number per floret: 1. Filament: Length: 1-2 mm. Color: 187B. Anther: Shape: Oval. Length: 1 mm. Color: 187B. Pollen: Color: 15B. Amount: Too much to quantify.

*Gynoecium*.—Presence: In disc and ray florets. Pistil length: 1-2 mm. Stigma: Shape: Two-parted. Color: 187B. Style: Length: 1-2 mm. Color: 187B.

*Seeds/fruit*.—Length: 1-2 mm. Color: 164C.

Disease/pest resistance:

*Disease resistance*.—No additional disease resistance has been observed beyond the typical resistance in *Echinacea* plants.

*Pest resistance*.—No additional pest resistance has been observed beyond the typical resistance in *Echinacea* plants.

Weather tolerance:

*Temperature tolerance*.—No additional temperature resistance has been observed beyond the typical resistance in *Echinacea* plants.

*Drought tolerance*.—No additional drought resistance has been observed beyond the typical resistance in *Echinacea* plants.

I claim:

1. A new and distinct cultivar of *Echinacea* plant named 'BullEchipur 118', as herein illustrated and described.

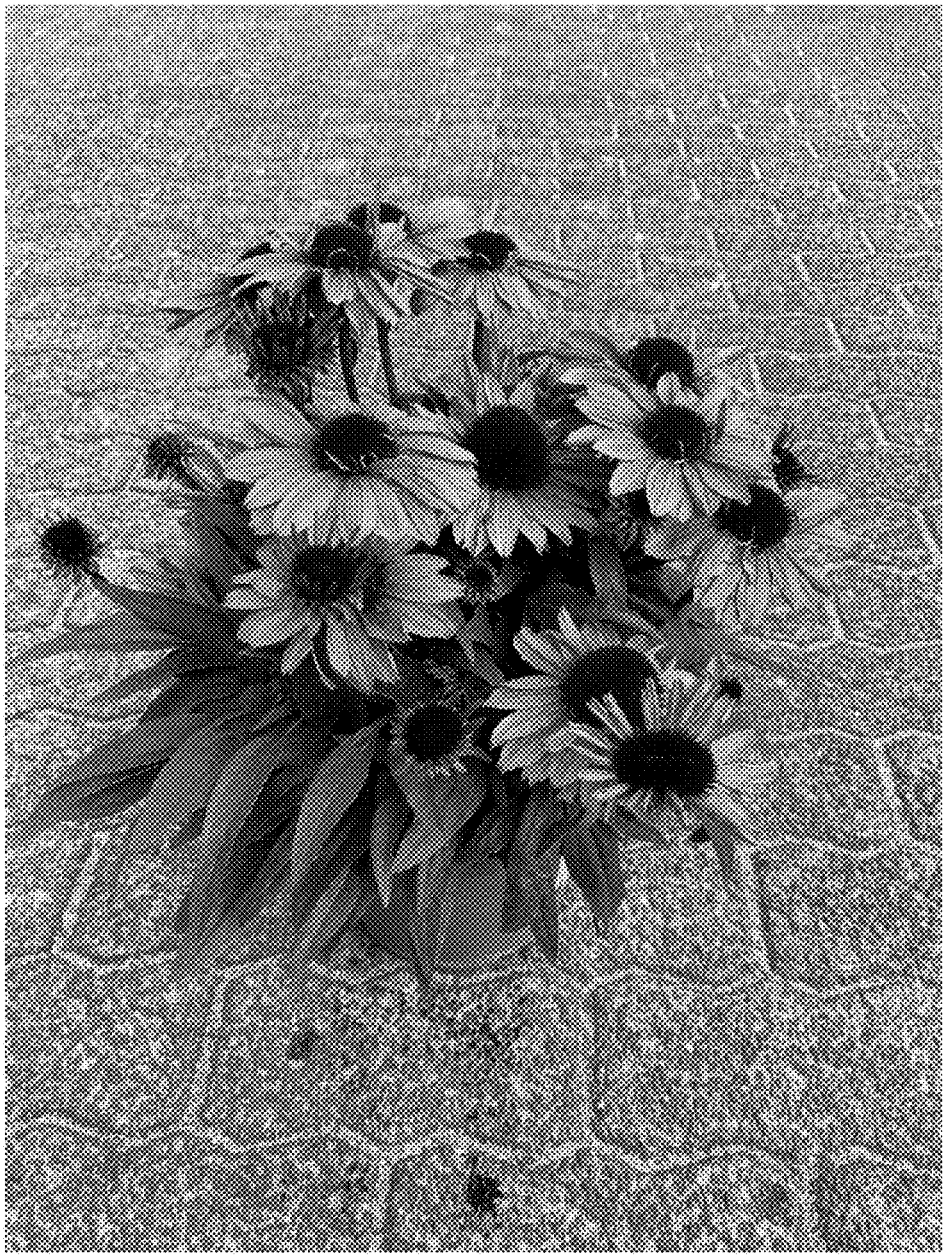

* * * * *